(12) United States Patent
Policello et al.

(10) Patent No.: US 10,188,102 B2
(45) Date of Patent: Jan. 29, 2019

(54) LOW FOAM SURFACTANT COMPOSITION AND METHODS OF MAKING THE SAME

(71) Applicant: Momentive Performance Materials Inc., Waterford, NY (US)

(72) Inventors: George A. Policello, Ossining, NY (US); Linh The Truong, Congers, NY (US); Benjamin Falk, Yorktown Heights, NY (US); Kalman Koczo, Suffern, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

(21) Appl. No.: 14/800,197

(22) Filed: Jul. 15, 2015

(65) Prior Publication Data

US 2017/0013830 A1    Jan. 19, 2017

(51) Int. Cl.

| | | |
|---|---|---|
| *A01N 25/30* | (2006.01) | |
| *A01N 57/20* | (2006.01) | |
| *A01N 39/04* | (2006.01) | |
| *B01D 19/04* | (2006.01) | |
| *C08G 65/336* | (2006.01) | |
| *C08L 71/02* | (2006.01) | |

(52) U.S. Cl.
CPC .............. *A01N 25/30* (2013.01); *A01N 39/04* (2013.01); *A01N 57/20* (2013.01); *B01D 19/0409* (2013.01); *C08G 65/336* (2013.01); *C08L 71/02* (2013.01)

(58) Field of Classification Search
None
See application file for complete search history.

(56) References Cited

U.S. PATENT DOCUMENTS

| | | |
|---|---|---|
| 3,159,601 A | 12/1964 | Ashby |
| 3,159,662 A | 12/1964 | Ashby |
| 3,220,972 A | 11/1965 | Lamoreaux |
| 3,715,334 A | 2/1973 | Karstedt |
| 3,775,452 A | 11/1973 | Karstedt |
| 3,814,730 A | 6/1974 | Karstedt |
| 5,558,806 A | 9/1996 | Policello et al. |
| 5,674,832 A | 10/1997 | Keys |
| 5,968,872 A | 10/1999 | Policello et al. |
| 6,221,922 B1 | 4/2001 | Policello et al. |
| 6,534,077 B2 | 3/2003 | Policello et al. |
| 6,890,886 B2 | 10/2005 | Policello et al. |
| 8,470,951 B2 | 6/2013 | Maliverney |
| 2014/0066405 A1 | 3/2014 | Nishimura et al. |

FOREIGN PATENT DOCUMENTS

| | | |
|---|---|---|
| CN | 103421035 A * | 12/2013 |
| WO | 2008111928 | 9/2008 |

OTHER PUBLICATIONS

Translation of CN103421035.*
J.L. Spier, "Homogeneous Catalysis of Hydrosilation by Transition Metals, In Advances in Organometallic Chemistry", vol. 17, (1979) pp. 407-447, F.G.A. Stone & R. West Editors, Academic Press.
Gaskin, et al., "Antagonism of the Foliar Uptake of Glyphosate into Grasses by Organosilicone Surfactants, Part 1: Effects of Plant Species, Formulation, Concentrations and Timing of Application", Pestic. Sci. 38 (1993) pp. 185-192.
Liu, Z. Q., "Influence of Surfactants on Foliar Uptake of Herbicides," The Proc. of the 18th Asian-Pacific Weed Sci. Soc. Conf., May 28-Jun. 2, 2001, pp. 561-566.
Written Opinion and International Search Report from PCT/US2016/037567 dated Sep. 1, 2016.

* cited by examiner

*Primary Examiner* — Abigail Vanhorn
*Assistant Examiner* — Luke E Karpinski
(74) *Attorney, Agent, or Firm* — Joseph S. Ostroff

(57) ABSTRACT

There is provided herein a low foam surfactant composition comprising:
(a) di-trisiloxane alkoxylate component of the general formula (I):

$$(R^1R^2R^3SiO)_2(R^4)Si\text{—}R^5\text{—}Si(R^6)(OSiR^7R^8R^9)_2 \quad \text{(I); and,}$$

(b) mono-trisiloxane alkoxylate component of the general formula (II):

$$(R^{12}R^{13}R^{14}SiO)_2Si(R^{15})R^{16} \quad \text{(II)}$$

wherein di-trisiloxane alkoxylate (I) is soluble in mono-trisiloxane alkoxylate and methods of making the same.

24 Claims, No Drawings

LOW FOAM SURFACTANT COMPOSITION AND METHODS OF MAKING THE SAME

FIELD OF THE INVENTION

There is provided herein a surfactant composition, more specifically a silicone surfactant composition that exhibits lower foam properties than known silicone surfactants.

BRIEF DESCRIPTION OF THE RELATED ART

Surfactants have been used widely in many fields. In the use of surfactants, properties such as wetting, spreading, foaming, detergency, and the like are important in the various applications in which they are employed. But, in some applications, such as agriculture, surfactants produce an undesirable level of foam. Some classes of surfactants have been found to produce very persistent foam, which is not easily controlled by conventional foam control agents, and therefore a low-foam version is desirable.

SUMMARY OF THE INVENTION in accordance with the invention there is provided herein a composition comprising a mixture of di-trisiloxane alkoxylate and mono-trisiloxane alkoxylate which has shown a surprising and unexpected decrease in foaming and improved spreadability as compared to solely mono-trisiloxane foam control agents.

More specifically, there is provided herein a low foam surfactant composition comprising:

a) di-trisiloxane alkoxylate of general formula (I)

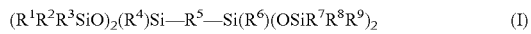  (I)

where $R^1$, $R^2$, $R^3$, $R^4$, $R^6$, $R^7$, $R^8$ and $R^9$ each independently is methyl, ethyl or linear or branched monovalent hydrocarbon radical of 3 or 4 carbon atoms, $R^5$ is a divalent polyalkyleneoxide group having the general structure:

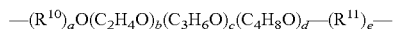

wherein $R^{10}$ and $R^{11}$ each independently is a linear or branched divalent hydrocarbon radical of from 2 to 6 carbon atoms, such as the non-limiting examples of ethyl, propyl and isobutyl, a and e each independently is 0 or 1, and b, c, and d each independently is 0 or greater, provided that $1 \le b+c+d \le 20$; and, b) mono-trisiloxane alkoxylate of general formula (II):

$(R^{12}R^{13}R^{14}SiO)_2Si(R^{15})R^{16}$  (II)

where each of $R^{12}$, $R^{13}$, $R^{14}$ and $R^{15}$ independently is a linear or branched monovalent hydrocarbon radical of 1 to 4 carbon atoms, and $R^{16}$ is a monovalent polyalkyleneoxide group having the general structure:

where —$R^{17}$ is a linear or branched divalent hydrocarbon radical of 2 to 6 carbon atoms, $R^{18}$ is selected from hydrogen, monovalent hydrocarbon radical of 1 to 4 carbon atoms or acetyl, and g, h and i each independently is 0 or greater, provided that $1 \le g+h+i \le 15$;

and, wherein di-trisiloxane alkoxylate (I) is soluble in mono-trisiloxane alkoxylate (II).

In addition, there is also provided a method of making the foregoing low foam surfactant composition, the method comprising combining a) di-trisiloxane alkoxylate of general formula (I):

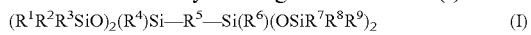  (I)

with b) mono-trisiloxane alkoxylate of general formula (II):

  (II)

wherein di-trisiloxane alkoxylate (I) is soluble in mono-trisiloxane alkoxylate component (II).

DETAILED DESCRIPTION OF THE INVENTION

The low foam surfactant composition described herein contains a di-trisiloxane alkoxylate (I) in combination with a mono-trisiloxane alkoxylate (II). The presence of the di-trisiloxane alkoxylate in the composition has been shown to have better foam-reduction properties, and similar or better spreadability as compared to solely mono-trisiloxane alkoxylates. Further, di-trisiloxane alkoxylate (I) herein has shown better compatibility with mono-trisiloxane alkoxylate surfactants (II) than conventional polydimethylsiloxane-based foam control agents and lower foam than conventional polydimethylsiloxane-based foam control agents. Some non-limiting examples of such conventional polydimethylsiloxane based foam control agents are the polysiloxane compounds having internal pendant and/or terminal monovalent polyalkylene oxide moieties.

Other than in the working examples or where otherwise indicated, all numbers expressing amounts of materials, reaction conditions, time durations, quantified properties of materials, and so forth, stated in the specification and claims are to be understood as being modified in all instances by the term "about" whether or not the term "about" is used in the expression.

It will be understood that any numerical range recited herein includes all sub-ranges within that range and any combination of the various endpoints of such ranges or sub-ranges, be it described in the examples or anywhere else in the specification.

It will also be understood herein that any of the components of the invention herein as they are described by any specific genus or species detailed in the examples section of the specification, can be used in one embodiment to define an alternative respective definition of any endpoint of a range elsewhere described in the specification with regard to that component, and can thus, in one non-limiting embodiment, be used to supplant such a range endpoint, elsewhere described.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

Reactants and components referred to by chemical name or formula in the specification or claims hereof, whether referred to in the singular or plural, may be identified as they exist prior to coming into contact with another substance referred to by chemical name or chemical type (e.g., another reactant or a solvent). Preliminary and/or transitional chemical changes, transformations, or reactions, if any, that take place in the resulting mixture, solution, or reaction medium may be identified as intermediate species, master batches, and the like, and may have utility distinct from the utility of the reaction product or final material. Other subsequent changes, transformations, or reactions may result from bringing the specified reactants and/or components together under the conditions called for pursuant to this disclosure. In these other subsequent changes, transformations, or reactions the reactants, ingredients, or the components to be brought together may identify or indicate the reaction product or final material.

In describing the products of the instant invention as a reaction product of initial materials reference is made to the initial species recited and it is to be noted that additional materials may be added to the initial mixture of synthetic precursors. These additional materials may be reactive or non-reactive. The defining characteristic of the instant invention is that the reaction product is obtained from the reaction of at least the components listed as disclosed. Non-reactive components may be added to the reaction mixture as diluents or to impart additional properties unrelated to the properties of the composition prepared as a reaction product. Thus for example particulate solids such as pigments may be dispersed into the reaction mixture, before during or after reaction to produce a reaction product composition that additionally comprises the non-reactive component, e.g., a pigment. Additional reactive components may also be added; such components may react with the initial reactants or they may react with the reaction product; the phrase "reaction product" is intended to include those possibilities as well as including the addition of non-reactive components.

As used herein in reference to a hydrocarbon radical, the term "monovalent" means that the radical is capable of forming one covalent bond per radical, the term "divalent" means that the radical is capable of forming two covalent bonds per radical and the term "trivalent" means that the radical is capable of forming three covalent bonds per radical. Generally, a monovalent radical can be represented as having been derived from a saturated hydrocarbon compound by conceptual removal of one hydrogen atom from the compound, a divalent radical can be represented as having been derived from a saturated hydrocarbon compound by conceptual removal of two hydrogen atoms from the compound and a trivalent radical can be represented as having been derived from a saturated hydrocarbon compound by conceptual removal of three hydrogen atoms from the compound. For example, an ethyl radical, that is, a —$CH_2CH_3$ radical, is a monovalent radical; a dimethylene radical, that is, a —$(CH_2)_2$— radical, is a divalent radical and an ethanetriyl radical, that is,

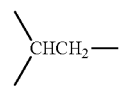

radical, is a trivalent radical, each of which can be represented as having been derived by conceptual removal of one or more hydrogen atoms from the saturated hydrocarbon ethane.

As used herein, the terminology "hydrocarbon radical" means a straight chain or branched hydrocarbon radical, preferably containing from 1 to 6 carbon atoms per radical, which may be saturated or unsaturated and which may be optionally substituted or interrupted with one or more atoms or functional groups, such as, for example, carboxyl, cyano, hydroxy, halo and oxy. Suitable monovalent hydrocarbon radicals may include, for example, alkyl, alkenyl, alkynyl, hydroxyalkyl, cyanoalkyl, carboxyalkyl, alkyloxy, oxaalkyl, alkylcarbonyloxaalkylene, carboxamide and haloalkyl, such as, for example, methyl, ethyl, sec-butyl, tert-butyl, ethenyl, propenyl, butynyl, hydroxypropyl, cyanoethyl, butoxy, carboxymethyl, chloromethyl and 3,3,3-fluoropropyl.

Suitable divalent hydrocarbon radicals include, for example, linear or branched alkylene radicals, such as, for example, methylene, dimethylene, trimethylene, ethylethylene, 2-methyltrimethylene, 2,2-dimethyltrimethylene and linear or branched oxalkylene radicals such as, for example, methyleneoxypropylene.

Suitable trivalent acyclic hydrocarbon radicals include, for example, alkanetriyl radicals, such as, for example, 1,1,2-ethanetriyl, 1,2,4-butanetriyl, 1,2,8-octanetriyl, 1,2,4-cyclohexanetriyl and oxaalkanetriyl radicals such as, for example, 1,2,6-triyl-4-oxahexane.

As used herein the term "alkyl" means a saturated straight or branched monovalent hydrocarbon radical. In a preferred embodiment, monovalent alkyl groups are selected from linear or branched alkyl groups containing from 1 to 6 carbons per group, such as, for example, methyl, ethyl, propyl, iso-propyl, n-butyl, iso-butyl, sec-butyl, tert-butyl, pentyl and hexyl.

As used herein the term "alkenyl" means a straight or branched monovalent terminally unsaturated hydrocarbon radical, preferably containing from 2 to 6 carbon atoms per radical, such as, for example, vinyl, ethenyl, allyl, 2-propenyl, 3-butenyl, and 5-hexenyl.

In one non-limiting embodiment herein, some specific non-limiting examples of hydrocarbon radicals that may be used herein are methyl, ethyl, vinyl, allyl, n-propyl, iso-propyl, n-butyl, isobutyl, tert-butyl, n-pentyl, iso-pentyl, neopentyl and tert-pentyl; hexyl, such as the n-hexyl group; and the 2,2,4-trimethylpentyl group.

The term "soluble" as used in the expression "wherein di-trisiloxane alkoxylate component 'a' is soluble in mono-trisiloxane alkoxylate (II) means that the low foam surfactant composition comprising components (I) and (II) forms either a clear solution or a hazy, but stable (i.e., not visibly gelling or precipitating for a period of from the formation of the composition up until 6 months, specifically up until 12 months and most specifically up until 18 months) at 25° C. temperature at sea level.

In accordance with the invention there is provided a low foam surfactant composition, as described herein, which comprises:

a. di-trisiloxane alkoxylate of general formula (I):

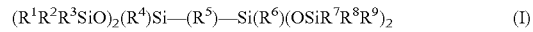

where $R^1$, $R^2$, $R^3$, $R^4$, $R^6$, $R^7$, $R^8$ and $R^9$ each independently is methyl, ethyl or a linear or branched monovalent hydrocarbon radical of 3 to 4 carbon atoms, $R^5$ is a divalent polyalkyleneoxide group having the general structure:

$$—(R^{10})_a O(C_2H_4O)_b(C_3H_6O)_c(C_4H_8O)_d—(R^{11})_e—$$

wherein $R^{10}$ and $R^{11}$ each independently is a linear or branched divalent hydrocarbon radical of from 2 to 6 carbon atoms, such as the non-limiting examples of ethyl, propyl and isobutyl, a and e each independently is 0 or 1, b, c, and d each independently is 0 or greater, provided that $1 \le b+c+d \le 20$; and, b. mono-trisiloxane alkoxylate of general formula (II):

$$(R^{12}R^{13}R^{14}SiO)_2Si(R^{15})—R^{16} \quad\quad (II),$$

where $R^{12}$, $R^{13}$, $R^{14}$ and $R^{15}$ each independently is a linear or branched monovalent hydrocarbon radical of 1 to 4 carbon atoms, and $R^{16}$ is a monovalent polyalkyleneoxide group having the general structure:

$$—R^{17}O(C_2H_4O)_g(C_3H_6O)_h(C_4H_8O)_i—R^{18}$$

where —$R^{17}$ is a linear or branched divalent hydrocarbon radical of 2 to 6 carbon atoms, $R^{18}$ is hydrogen, vinyl, allyl, methallyl, propenyl, a monovalent hydrocarbon radical of 1 to 4 carbon atoms or acetyl, and g, h and i, each independently is 0 or greater, provided that $1 \le b+c+d \le 15$; and, wherein di-trisiloxane alkoxylate (I) is soluble in mono-trisiloxane alkoxylate (II).

In one non-limiting embodiment, in formula (I), b, c and d are such that $1 \le b+c+d \le 20$, more specifically, $2 \le b+c+d \le 15$ and still more specifically, $4 \le b+c+d \le 10$. In one other embodiment, $1 \le b+c+d \le 20$, more specifically, $2 \le b+c+d \le 15$ and still more specifically, $7 \le b+c \le 10$.

In another non-limiting embodiment, in formula (II), g, h and i are such that $1 \le g+h+i \le 15$, more specifically, $2 \le g+h+i \le 10$ and still more specifically, $4 \le g+h+i \le 8$. In another embodiment, g, h and i are such that $1 \le g+h \le 5$, more specifically, $2 \le g+h \le 10$, and still more specifically, $4 \le +h \le 8$.

One specific embodiment herein is a low foam surfactant composition comprising di-trisiloxane alkoxylate component (a) of the general formula (I) wherein $R^1$, $R^2$, $R^3$, $R^4$, $R^6$, $R^7$, $R^8$ and $R^9$ are methyl; divalent polyalkyleneoxide group $R^5$ is such that $R^{10}$ and $R^{11}$ each independently is a hydrocarbon radical of 3 or 4 carbons, such as the non-limiting examples of propyl and isobutyl; a and e are 1, b is 4 to 6, c is 1.5 to 3, and d is 0 or 1; and, mono-trisoloxane alkoxylate component (II) wherein $R^{12}$, $R^{13}$, $R^{14}$ and $R^{15}$ are methyl, $R^{17}$ is a hydrocarbon radical of 3 or 4 carbon atoms; $R^{18}$ is hydrogen; g is 4 to 6, h is 1.5 to 3, and i is 0.

In another specific embodiment herein, there is provided a low foam surfactant wherein in formula (I), $R^1$, $R^2$, $R^3$, $R^4$, $R^6$, $R^7$, $R^8$ and $R^9$ are each methyl, divalent polyalkyleneoxide group $R^5$ is such that $R^{10}$ and $R^{11}$ each independently is a hydrocarbon radical of 3 or 4 carbon atoms, a and e are 1, b is 0 or 1, c is 1 to 8 and preferably 1 to 4, and d is 0 or 1; and, wherein in formula (II), $R^{12}$, $R^{13}$, $R^{14}$ and $R^{15}$ are methyl, $R^{17}$ is a hydrocarbon radical of 3 or 4 carbon atoms, $R^{18}$ is hydrogen, g is 4 to 6, h is 1.5 to 3 and i is 0.

In yet another specific embodiment there is provided a low foam surfactant composition wherein in component (I), $R^1$, $R^2$, $R^3$, $R^4$, $R^6$, $R^7$, $R^8$ and $R^9$ are methyl, divalent polyalkyleneoxide group $R^5$ is such that $R^{10}$ and $R^{11}$ each independently is a hydrocarbon radical of 3 or 4 carbon atoms, a and e are 1, b is 1 to 4, c is 0 or 1 and d is 0 or 1; and, wherein in component (II) $R^{12}$, $R^{13}$, $R^{14}$ and $R^{15}$ are methyl, $R^{17}$ is a hydrocarbon radical of 3 or 4 carbon atoms, $R^{18}$ is hydrogen, g is 4 to 6, h is 1.5 to 3 and i is 0.

Another specific embodiment herein is a low foam surfactant composition comprising component (I) wherein $R^1$, $R^2$, $R^3$, $R^4$, $R^6$, $R^7$, $R^8$ and $R^9$ are methyl; divalent polyalkyleneoxide group $R^5$ is such that $R^{10}$ and $R^{11}$ each independently is a hydrocarbon radical of 3 or 4 carbon atoms; a and e are 1, b is 4 to 8, c is 1.5 to 3, and d is 0 to 1; and, component (II) wherein $R^{12}$, $R^{13}$, $R^{14}$ and $R^{15}$ are methyl, $R^{17}$ is a hydrocarbon radical of 3 or 4 carbon atoms; $R^{18}$ is hydrogen; g is 6 to 8 and h and i are 0.

Another specific embodiment herein is a low foam surfactant composition comprising di-trisiloxane alkoxylate (I) wherein $R^1$, $R^2$, $R^3$, $R^4$, $R^6$, $R^7$, $R^8$ and $R^9$ are methyl; divalent polyalkyleneoxide group $R^5$ is such that a and e are 0; b is 4 to 8, c is 1.5 to 3, and d is 0 or 1; and, mono-trisiloxane alkoxylate (II) wherein $R^{12}$, $R^{13}$, $R^{14}$ and $R^{15}$ are methyl, $R^{17}$ is a hydrocarbon radical of 3 or 4 carbon atoms; $R^{18}$ is hydrogen; g is 6 to 8, and h and i are each 0.

Another specific embodiment herein is a low foam surfactant composition comprising di-trisiloxane alkoxylate (I) wherein $R^1$, $R^2$, $R^3$, $R^4$, R, $R^7$, $R^8$ and $R^9$ are methyl; divalent polyalkyleneoxide group $R^5$ is such that $R^{10}$ and $R^{11}$ each independently is a hydrocarbon radical of 3 or 4 carbon atoms, b is 6 to 9, c and d are each 0; and, mono-trisiloxane alkoxylate (II) wherein $R^{12}$, $R^{13}$, $R^{14}$ and $R^{15}$ are methyl, $R^{17}$ is a hydrocarbon radical of 3 or 4 carbon atoms; $R^{18}$ is hydrogen; g is 6 to 8, and h and i are each 0.

Another specific embodiment herein is a low foam surfactant composition comprising di-trisiloxane alkoxylate (I) wherein $R^5$ is of the general structure:

$$—(CH_2CHR^{25}CH_2)_a—O(C_2H_4O)_b(C_3H_6O)_c—(CH_2CHR^{26}CH_2)_e—$$

where a, b, c and e are as defined herein, and $R^{25}$ and $R^{26}$ each independently is hydrogen or methyl, and more specifically, b is 0 or 4 to about 10, c is 0 or 2 to about 9, and more specifically, a is 1, b is 5, c is 2.5 and e is 0 and $R^2$ and $R^{28}$ are hydrogen.

As described above there is provided herein a method of making the low foam surfactant composition comprising combining component (a) of the general formula (I) with component (b) of the general formula (II), wherein component (a) is soluble in the component (b).

Methods of combining the components (a) and (b) are well known by those skilled in the art, such as manual or machine mixing using known or conventional apparatus. The di-trisiloxane alkoxylate component (a) of the present invention may be made separately and then physically mixed with mono-trisiloxane alkoxylate component (b), to make the low foam surfactant composition of the present invention, or it may be made in-situ along with the mono-trisiloxane alkoxylate component (b) (as a 1-pot reaction).

In one embodiment herein component (a) is made by a dehydrocondensation reaction and/or a hydrosilylation reaction. Some embodiments could comprise using both dehydrocondensation reactions and hydrosilylation reactions consecutively or concurrently. Dehydrocondensation and hydrosilylation reaction conditions such as reaction time, temperature and pressure are well known by those skilled in the art.

In another embodiment herein, component (b) is made by a hydrosilylation reaction.

Typical dehydrocondensation catalysts may be selected from, but not limited to, sodium propionate, sodium acetate, sodium hydroxide, potassium hydroxide, cesium hydroxide, sodium methoxide, potassium methoxide, cesium methoxide sodium t-butoxide, potassium t-butoxide, cesium t-butoxide, sodium t-amylate, potassium t-amylate and cesium t-amylate, and the like.

Hydrosilylation reactions are well understood by those skilled in the art and generally comprise the reaction between two reactive moieties, one being a Si—H moiety and the other being an unsaturated moiety, which is catalyzed by a precious metal catalyst, such as the non-limiting examples of a platinum catalyst.

Precious metal catalysts suitable for making polyalkyleneoxide modified organosilicones are also well known in the art and comprise complexes of rhodium, ruthenium, palladium, osmium, Iridium, or platinum. Many types of platinum catalysts for this Si—H olefin addition reaction are known and such platinum catalysts may be used to generate the compositions of the present invention. The platinum compound can be selected from those having the formula (PtCl$_2$Olefin) and H(PtCl$_3$Olefin) as described in U.S. Pat. No. 3,159,601, hereby incorporated by reference in its entirety. A further platinum-containing material can be a complex of chloroplatinic acid with up to 2 moles per gram of platinum of a member selected from the class consisting of alcohols, ethers, aldehydes and mixtures thereof as described in U.S. Pat. No. 3,220,972 hereby incorporated by reference in its entirety. Yet another group of platinum-containing materials useful in this present invention is described in U.S. Pat. Nos. 3,715,334; 3,775,452 and 3,814,730 (Karstedt), the contents of all of which are incorporated by reference herein in their entireties. Additional background concerning the art may be found in J. L. Spier, "Homogeneous Catalysis of Hydrosilation by Transition Metals", in Advances in Organometallic Chemistry, volume 17, pages 407 through 447, F. G. A. Stone and R. West editors, published by Academic Press (New York, 1979). Those skilled in the art can easily determine an effective amount of platinum catalyst.

Generally an effective amount ranges from about 0.1 to 50 parts per million of the total polyalkyleneoxide modified organosilicone composition, or in this specific case, polyalkyleneoxide-modified heptamethyltrisiloxane.

In one embodiment herein mono-trisiloxane alkoxylate (II) can be made by a hydrosilylation reaction of an alkene-terminated polyether of the general formula:

$$R^{17*}-O-(C_2H_4O)_g(C_3H_6O)_h(C_4H_8O)_i-R^{18}$$

wherein $R^{17*}$ is an alkene-terminated olefinic group of from 2 to about 6 carbon atoms, $R^{18}$ is hydrogen, a monovalent hydrocarbon radical of from 1 to about 4 carbon atoms, or acetyl, and g, h and i each independently is 0 or greater, provided that $1 \leq g+h+i \leq 15$, more specifically as g, h and i are described elsewhere herein, with 1,1,1,3,5,5,5-heptaalkyltrisiloxane wherein the alkyl group contains from 1 to about 4 carbon atoms, in the presence of a hydrosilylation catalyst. The amounts of alkene-terminated polyether and heptaalkyltrisiloxane are such that the molar ratio of the amount of Si—H moieties in the heptaalkyltrisiloxane to hydroxyl moieties in the alkene-terminated polyether are from about 0.9:1 to about 1.1:1.

In another specific embodiment the component (b) reaction product of such a reaction is monotrisiloxane alkoxylate of the general formula:

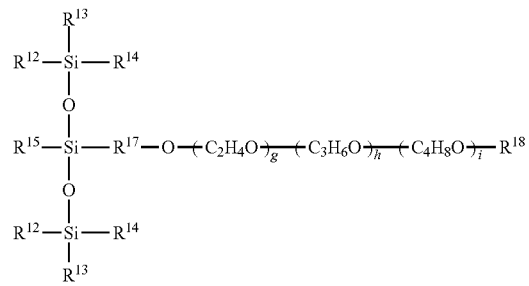

wherein each of $R^{12}$, $R^{13}$, $R^{14}$ and $R^{15}$ are methyl, ethyl or a linear or branched monovalent hydrocarbon radical of 3 or 4 carbon atoms, $R^{17}$ is a divalent hydrocarbon radical of 2 to 6 carbon atoms, $R^{18}$ is hydrogen, vinyl, allyl, methallyl, propenyl or a monovalent hydrocarbon radical of 1 to 4 carbon atoms and g, h, and i each independently is zero or greater, provided that $1 \leq g+h+i \leq 15$.

As described above, in one embodiment, component (a) of general formula (I) is made by a hydrosilylation reaction, which can comprise, in one embodiment, reacting diolefinically-modified polyalkylene oxide intermediate of the general formula (V):

$$R^{22}O(C_2H_4O)_k(C_3H_6O)_m(C_4H_8O)_p-R^{23} \quad (V)$$

where k, m and p are $\geq 0$ provided that $1 \leq k+m+p \leq 20$, more specifically $2 \leq k+m+p \leq 15$ and still more specifically $4 \leq k+m+p \leq 8$, and where $R^{22}$ and $R^{23}$ are independently selected from an olefinically modified group of the general structure:

$$CH_2=C(R^{24})-(CH_2)_r-$$

where $R^{24}$ is hydrogen or methyl and r is 0 to 4, with 1,1,1,3,5,5,5-heptaalkyltrisiloxane wherein the alkyl groups independently contain from 1 to 4 carbon atoms in the presence of a hydrosilylation catalyst. In one embodiment, such a reaction produces component (a) of the general formula (I) and the method can then further comprise the mixing of component (a) of the general formula (I) with a component (b) of the general formula (II) to produce the low foam surfactant composition.

In one embodiment, the hydrosilylation of heptaalkyltrisiloxane with the di-olefinically modified polyalkyleneoxide intermediate (V) in the presence of a hydrosilylation catalyst, results in a reaction product wherein the heptaalkyltrisiloxane is attached to polyalkyleneoxide via a Si—C linkage. In one embodiment, the amount of heptaalkyltrisiloxane and di-olefinically modified polyalkyleneoxide intermediate (V) are such that there is from about 1.9 to about 2.1 moles of heptaalkyltrisiloxane to each mole of di-olefinically modified polyalkyleneoxide intermediate (V).

Alternatively, the hydrosilylation reaction of formula (V) with 1,1,1,3,5,5,5-heptaalkyltrisiloxane can further comprises the presence of a mono alkenyl-terminated polyalkylene oxide component of the general formula (VI):

$$CH_2=C(R^{21})-(CH_2)_rO-(C_2H_4O)_k(C_3H_6O)_m(C_4H_8O)_p-H \quad (VI)$$

where $R^{21}$ is hydrogen or methyl, and k, m and p are 20 provided that $1 \leq k+m+p \leq 20$, and k, m and p are as defined elsewhere herein, and r is 0 to 4, and wherein the reaction produces a mixture of component (a) of general formula (I) and component (b) of general formula (II). Such an in-situ production of the low foam surfactant composition herein by hydrosilylation of heptaalkyltrisiloxane with a blend of the di-olefinically modified polyalkyleneoxide intermediate (V)

and a mono-olefinically polyalkyleneoxide intermediate (VI) yields components (I) and (II) at a desired concentration.

When made in-situ, the di-trisiloxane alkoxylate component (I) of the present invention is present in the mixture of a di-trisiloxane alkoxylate (I) and mono-trisiloxane alkoxylate (II) at a ratio of 0.05:1 to 19:1, more specifically from about 0.05:1 to about 1:1. In one embodiment, the amount of heptaalkyltrisiloxane, di-olefinically modified polyalkyleneoxide intermediate (V) and mono alkenyl-terminated polyalkylene oxide (VI) are such that the amount of silyl-hydride in the heptaalkyltrisiloxane as compared to the total amount of unsaturation in formulae (V) and (VI) are about equivalent. In another embodiment, there is from about 5 mole % to about 35 mole % extra silyl-hydride moieties from the heptaalkyltrisiloxane relative to the total amount of unsaturation in formulae (V) and (VI).

In yet another embodiment, there is from about 5 mole % to about 35 mole % extra unsaturated polyalkyleneoxide intermediate relative to the heptaalkyltrisiloxane in formulae (V) and (VI).

In one further embodiment, such a reaction mixture of formula (V), 1,1,1,3,5,5,5-heptaalkyltrisiloxane and mono alkenyl-terminated polyalkylene oxide component of general formula (VI) and heptaalkyltrisiloxane can comprise an excess of silyl-hydride moiety in 1,1,1,3,5,5,5-heptaalkyltrisiloxane to total unsaturated moiety in (V) and (VI) as described above, and also a dehydrocondensation catalyst, such as the non-limiting example of sodium propionate, wherein such excess 1,1,1,3,5,5,5-heptaalkyltrisiloxane can react with the terminal hydroxyl groups of formula (VI) in a dehydrocondensation reaction to produce a mixture of component (a) of the general formula (I) and component (b) of the general formula (II) to provide the low foam surfactant composition herein.

In one non-limiting embodiment, the diolefinically-modified polyalkylene oxide intermediate of general formula (V) is made by reacting a molecule of general formula (III):

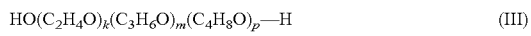

$HO(C_2H_4O)_k(C_3H_6O)_m(C_4H_8O)_p$—H    (III)

wherein k, m and p are each 20 provided that 1≤k+m+p≤20, more specifically, 2≤k+m+p≤15, still more specifically where ≤4k+m+p≤8, with between 2 and 2.5 equivalents, of an alkenyl halide having the general formula:

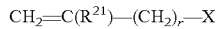

$CH_2$=$C(R^{21})$—$(CH_2)_r$—X where $R^{21}$ hydrogen or methyl r is 0 to 4; and, X is selected from Cl, Br or I, in the presence of a base.

Further, the diolefinically-modified polyalkylene oxide intermediate of general formula (V) can be made by reacting a molecule of general formula (IV):

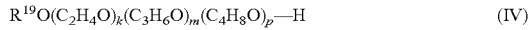

$R^{19}O(C_2H_4O)_k(C_3H_6O)_m(C_4H_8O)_p$—H    (IV)

wherein $R^{19}$ is $CH_2$=$CH(R^{20})$—$(CH_2)_q$—; $R^{20}$ is hydrogen or methyl; and, q is 0 to 4, with an alkenyl halide having the general formula:

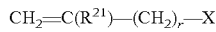

$CH_2$=$C(R^{21})$—$(CH_2)_r$—X where $R^{21}$ is hydrogen or methyl r is 0 to 4; and, X is selected from Cl, Br or I, in the presence of a base. Some non-limiting examples of a base are sodium or potassium hydroxide, or alkoxides of sodium, potassium and cesium. The reaction of a molecule of general formula (IV) with alkenyl halide is such that there is from about 1.0:1.1 to about 1.0:1.5 of moles of (IV) to alkenyl halide, preferably from about 1.0:1.1 to about 1.0:1.35. In one embodiment, formula (IV) and the formula of the alkene-terminated polyether described above can be used interchangeably herein.

As stated above, component (a) of general formula (I) can be made by a dehydrocondensation reaction and/or a hydrosilylation reaction as described herein.

In one non-limiting embodiment herein, the dehydrocondensation reaction is understood to be the reaction of polyalkyleneoxide intermediate (III) as described herein, or a hydroxyl-terminated heptaalkyltrisiloxane polyalkyleneoxide (b) (e.g. the alkene-terminated polyether described above), wherein the alkyl groups independently contain from 1 to 4 carbon atoms, e.g., heptamethyltrisiloxane polyalkyleneoxide, with between 0.05 and 2.1 equivalents of heptaalkyltrisiloxane, preferably from about 1.9 to about 2.1 equivalents, depending on the desired degree of conversion, in the presence of a dehydrocondensation catalyst to give a product where the heptaalkyltrisiloxane is attached to the polyalkyleneoxide via a Si—O—C linkage.

In another specific embodiment, the dehydrocondensation reaction comprises the reaction of a hydroxyl-terminated polyalkylene oxide intermediate of general formula (III):

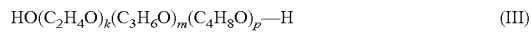

$HO(C_2H_4O)_k(C_3H_6O)_m(C_4H_8O)_p$—H    (III)

wherein k, m and p are ≥0 provided that 1≤k+m+p≤20, more specifically, 2≤k+m+p≤15, still more specifically 4≤k+m+p≤8, with 1,1,1,3,5,5,5-heptaalkyltrisiloxane wherein the alkyl groups independently contain from 1 to 4 carbon atoms, in the presence of a dehydrocondensation catalyst. In some embodiments, 1≤k+m≤20, more specifically, 2≤k+m≤15 and still more specifically 4≤k+m≤8, such as the non-limiting example of between 7 and 8.

In another embodiment, the reaction of a hydroxyl-terminated polyalkylene oxide intermediate of general formula (III) with 1,1,1,3,5,5,5-heptaalkyltrisiloxane is such that the 1,1,1,3,5,5,5-heptaalkyltrisiloxane is present in an excess molar amount relative to the hydroxyl-terminated polyalkylene oxide intermediate of general formula (III), the reaction producing di-trisiloxane alkoxylate component (a) of the general formula (I). In some other embodiments, such excess molar amounts can be from 5 to about 50% molar amount excess of silyl-hydride in heptaalkyltrisiloxane to total amount of hydroxyl moiety in formula (III). In another embodiment, the mono-trisiloxane alkoxylate component (b) of general formula (II) so-formed can be mixed with a component (a) of general formula (I).

In another embodiment, dehydrocondensation reaction comprises the reaction of a mono-trisiloxane alkoxylate component (b) of general formula (II) wherein $R^{18}$ is hydrogen with 1,1,1,3,5,5,5-heptaalkyltrisiloxane wherein the alkyl groups independently contain from 1 to 4 carbon atoms, in the presence of dehydrocondensation catalyst to produce component (a) of general formula (I) which is optionally further mixed with a component (b) of general formula (II) to provide the low foam surfactant composition. In one embodiment, such mono-trisiloxane alkoxylate component (b) can be the reaction product of the alkene-terminated polyether and heptaalkyltrisiloxane described above.

In one embodiment herein, the low foam surfactant composition is such that component (a) is present in an amount of from about 5 weight % to about 95 weight %, more specifically from about 10 weight % to about 30 weight %, and component (b) is present in an amount of from 5 weight % to about 95 weight %, more specifically from 70 weight % to about 90 weight %, based on the combined weight of components (a) and (b).

In another embodiment, any of the aforestated ranges of amounts of component (a) can have a lower endpoint, e.g., of 6, 8, 9, 11, 13, 15, 18 or 20 weight %, and independent of said lower endpoint, component (a) can have an upper endpoint, e.g., of 90, 94, 96, 97, 98 or 99 weight %.

In another embodiment, any of the aforestated ranges of amounts of component (b) can have a lower endpoint, e.g., of 6, 8, 9, 11, 13, 15, 18 or 20 weight %, and independent of said lower endpoint, component (b) can have an upper endpoints, e.g., of 90, 94, 96, 97, 98 or 99 weight %.

The low foam surfactant composition described herein can have a level of foam that is less than a surfactant composition that contains only mono-trisiloxane alkoxylate component (b), specifically, at least 10% less, more specifically at least 20% less and still more specifically at least 50% less, as measured by the sparge test described below.

The low foam surfactant composition described herein can have a level of foam that is less than about 1,000 ml of foam, more specifically less than about 800 ml of foam, more specifically less than about 500 ml of foam and most specifically less than about 300 ml of foam when 200 ml of a 0.1 wt % amount of the low foam surfactant composition is added to a 2 L graduated cylinder where the solution was subject to a nitrogen sparge through the solution through a stainless steel frit at a rate of 1 L per minute for one minute. In addition, such low levels of foam can comprise levels of less than 200 ml, less than 100 ml and less than 50 ml when tested in the same manner as stated above. Any of such ranges of foam stated herein can have lower endpoints of any one of 0, 1, 5, 10, 15, 20, 50, 75 or 100 ml of foam when tested in the same manner as stated above. Such measurements of lower levels of foam can be measured initially upon completion of the testing manner indicated above, at 1 minute thereafter, 2 minutes thereafter, or 5 minutes thereafter. Further, such measurements of lower levels of foam can be present for any of the concentrations of component (a) and component (b) as described herein.

The low foam surfactant composition described herein can have a level of spreadability that is similar to the spreadability of a surfactant composition that comprises only mono-trisiloxane alkoxylate component (b). The low foam surfactant composition described herein can have a spread diameter of from 20 mm to 50 mm, more specifically from 23 mm to 48 mm, even more specifically from 25 mm to 45 mm, and most specifically from 25 mm to 44 mm. Such measurements of spread diameter can be for any one of 0.05, 0.1, and 0.2 through 0.4 weight percent of the low foam surfactant composition in deionized water where a 10 micro-liter drop is placed on a polystyrene surface of a Petri dish and the spread diameter was measured after 30 seconds. Further, such measurements of spreadability can be present for any of the concentrations of component (a) and component (b) as described herein, but more specifically is for a concentration of component (a) of less than 20 wt % based on the combined weight of component (a) and component (b).

In addition, the low foam surfactant composition herein has a positive effect (i.e., increase) in the uptake of agrochemical compositions into plants and/or crops, such as the non-limiting examples of $^{14}C$-2,4-D dimethylamine salt into canola leaf as determined at 2 and 24 hours after treatment (HAT) according to the method described in Pro. 18th Asian-Pacific Weed Sci. Soc. Conf., pp. 561-566. Liu, Z Q; 2001. Influence of surfactants on foliar uptake of herbicides. In one embodiment, the uptake of $^{14}C$-2,4-D dimethylamine salt into canola leaf as determined at 2 HAT according to the method of Liu. described above ranges from about 8.0% to about 17% using a 1% a.e./100 L/ha; and at 24 HAT from about 58% to about 63% using a 1% a.e./100 L/ha.

Furthermore, the low foam surfactant composition herein has a positive effect (i.e., increase) on the efficacy (Spray application) of glyphosate on *Abutilion theophrasti* at 14 Days After Treatment (DAT) relative to just the mono-trisiloxane component (b) described herein. Some non-limiting examples of such an increase is from about 1 to about 80% increase, more specifically from about 20% to about 80% and most specifically from about 30% to about 80% control of velvetleaf by glyphosate at 7 and 14 DAT relative to just mono-trisiloxane component (b) described herein.

The compositions of the present invention may be utilized in a variety of forms: as liquid solutions, dispersions of solids in liquids, dispersions of liquids in liquids as the previously described emulsions, solid mixtures or solid solutions either separately or in the forms previously listed in combination one with the other.

In one embodiment herein there is provided any one or more of an agrochemical composition, coating composition, personal care composition, home care composition and oil or gas application comprising the low foam surfactant composition described herein.

Agrochemical Applications

Pesticide—Agriculture, Horticulture, Turf, Ornamental and Forestry:

Many pesticide applications require the addition of an adjuvant to the spray mixture to provide wetting and spreading on foliar surfaces. Often that adjuvant is a surfactant, which can perform a variety of functions, such as increasing spray droplet retention on difficult to wet leaf surfaces, enhance spreading to improve spray coverage, or to provide penetration of the herbicide into the plant cuticle. These adjuvants are provided either as a tank-side additive or used as a component in pesticide formulations.

Typical uses for pesticides include agricultural, horticultural, turf, ornamental, home and garden, veterinary and forestry applications. The pesticidal compositions of the present invention also include at least one pesticide, where the Low Foam Trisiloxane Alkoxylate composition of the present invention is present at an amount sufficient to deliver between 0.005% and 2% to the final use concentration, either as a concentrate or diluted in a tank mix. Optionally the pesticidal composition may include excipients, cosurfactants, solvents, foam control agents, deposition aids, drift retardants, biologicals, micronutrients, fertilizers and the like. The term pesticide means any compound used to destroy pests, e.g., rodenticides, insecticides, miticides, fungicides, and herbicides. Illustrative examples of pesticides that can be employed include, but are not limited to, growth regulators, photosynthesis inhibitors, pigment inhibitors, mitotic disrupters, lipid biosynthesis inhibitors, cell wall inhibitors, and cell membrane disrupters. The amount of pesticide employed in compositions of the invention varies with the type of pesticide employed. More specific examples of pesticide compounds that can be used with the compositions of the invention are, but not limited to, herbicides and growth regulators, such as: phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, glufosinate, sulfonylureas, imidazolinones, clethodim, diclofop-methyl, fenoxaprop-ethyl, fluazifop-p- butyl, haloxyfop-methyl, quizalofop, sethoxydim, dichlobenil, isoxaben, bipyridylium compounds, dicamba and tembotrione.

Fungicide compositions that can be used with the present invention include, but are not limited to, aldimorph, tridemorph, dodemorph, dimethomorph; flusilazol, azaconazole, cyproconazole, epoxiconazole, furconazole, propiconazole, tebuconazole and the like; imazalil, thiophanate, benomyl carbendazim, chlorothialonil, dicloran, trifloxystrobin, fluoxystrobin, dimoxystrobin, azoxystrobin, furcaranil, prochloraz, flusulfamide, famoxadone, captan, maneb, mancozeb, dodicin, dodine, and metalaxyl.

Insecticides, including larvacide, miticide and ovacide compounds that can be used with the composition of the present invention, but not limited to, *Bacillus thuringiensis*, spinosad, abamectin, doramectin, lepimectin, pyrethrins, carbaryl, primicarb, aldicarb, methomyl, amitraz, boric acid, chlordimeform, novaluron, bistrifluron, triflumuron, diflubenzuron, imidacloprid, diazinon, acephate, endosulfan, kelevan, dimethoate, azinphos-ethyl, azinphos-methyl, izoxathion, chlorpyrifos, clofentezine, lambda-cyhalothrin, permethrin, bifenthrin, cypermethrin and the like.

Fertilizers and Micronutrients:

Fertilizers or micronutrients include, but not limited to, zinc sulfate, ferrous sulfate, ammonium sulfate, urea, urea ammonium nitrogen, ammonium thiosulfate, potassium sulfate, monoammonium phosphate, urea phosphate, calcium nitrate, boric acid, potassium and sodium salts of boric acid, phosphoric acid, magnesium hydroxide, manganese carbonate, calcium polysulfide, copper sulfate, manganese sulfate, iron sulfate, calcium sulfate, sodium molybdate, and calcium chloride.

The pesticide or fertilizer may be a liquid or a solid. If a solid, it is preferable that it is soluble in a solvent, or the low foam surfactant composition of the present invention, prior to application, and the silicone may act as a solvent, or surfactant for such solubility or additional surfactants may perform this function.

Agricultural Excipients:

Buffers, preservatives and other standard excipients known in the art also may be included in the composition.

Solvents may also be included in the agrochemical compositions of the present invention. These solvents are in a liquid state at room temperature. Examples include water, alcohols, aromatic solvents, oils (i.e. mineral oil, vegetable oil, silicone oil, and so forth), lower alkyl esters of vegetable oils (i.e. for example, but not limited to methyl esters of soybean or canola oil), fatty acids, ketones, glycols, polyethylene glycols, diols, paraffinics, and so forth. Particular solvents would be 2,2,4 trimethyl, 1 3 pentane diol and alkoxylated (especially ethoxylated) versions thereof as illustrated in U.S. Pat. No. 5,674,832 herein incorporated by reference, or n-methyl-pyrrilidone.

Cosurfactants:

Cosurfactants useful herein include nonionic, cationic, anionic, amphoteric, zwitterionic, polymeric surfactants, or any mixture thereof. Surfactants are typically hydrocarbon based, silicone based or fluorocarbon based.

Moreover, other cosurfactants, that have short chain hydrophobes that do not interfere with superspreading as described in U.S. Pat. No. 5,558,806 herein incorporated by reference are also useful.

Useful surfactants include alkoxylates, especially ethoxylates, containing block copolymers including copolymers of ethylene oxide, propylene oxide, butylene oxide, and mixtures thereof; alkylarylalkoxylates, especially ethoxylates or propoxylates and their derivatives including alkyl phenol ethoxylate; arylarylalkoxylates, especially ethoxylates or propoxylates. and their derivatives; amine alkoxylates, especially amine ethoxylates; fatty acid alkoxylates; fatty alcohol alkoxylates; alkyl sulfonates; alkyl benzene and alkyl naphthalene sulfonates; sulfated fatty alcohols, amines or acid amides; acid esters of sodium isethionate; esters of sodium sulfosuccinate; sulfated or sulfonated fatty acid esters; petroleum sulfonates; N-acyl sarcosinates; alkyl polyglycosides; alkyl ethoxylated amines; and so forth.

Specific examples include alkyl acetylenic diols (SURFONYL—Air Products), pyrrilodone based surfactants (e.g., SURFADONE—LP 100—Ashland), 2—ethyl hexyl sulfate, isodecyl alcohol ethoxylates (e.g., RHODASURF DA 530—Rhodia), ethylene diamine alkoxylates (TETRONICS—BASF), ethylene oxide/propylene oxide copolymers (PLURONICS—BASF), Gemini type surfactants (Rhodia) and diphenyl ether Gemini type surfactants (e.g. DOWFAX—Dow Chemical).

Preferred surfactants include ethylene oxide/propylene oxide copolymers (EO/PO); amine ethoxylates; alkyl polyglycosides; oxo-tridecyl alcohol ethoxylates, and so forth.

In a more specific embodiment, the agrochemical composition of the present invention further comprises one or more agrochemical ingredients. Suitable agrochemical ingredients include, but not limited to, herbicides, insecticides, growth regulators, fungicides, miticides, acaricides, fertilizers, biologicals, plant nutritionals, micronutrients, biocides, paraffinic mineral oil, methylated seed oils (i.e. methylsoyate or methylcanolate), vegetable oils (such as soybean oil and canola oil), water conditioning agents such as Choice® (Loveland Industries, Greeley, Colo.) and Quest® (Helena Chemical, Collierville, Tenn.), modified clays such as Surround® (NovaSource, Phoenix, Ariz.), foam control agents, surfactants, wetting agents, dispersants, emulsifiers, deposition aids, antidrift components, and water.

Suitable agrochemical compositions are made by combining, in a manner known in the art, such as, by mixing one or more of the above components with the low foam surfactant composition of the present invention, either as a tank-mix, or as an "In-can" formulation. The term "tank-mix" means the addition of at least one agrochemical to a spray medium, such as water or oil, at the point of use. The term "In-can" refers to a formulation or concentrate containing at least one agrochemical component. The "In-can" formulation may then diluted to use concentration at the point of use, typically in a Tank-mix, or it may be used undiluted.

Coating Applications

Typically coatings formulations will require a wetting agent or surfactant for the purpose of emulsification, compatibilization of components, leveling, flow and reduction of surface defects. Additionally, these additives may provide Improvements in the cured or dry film, such as improved abrasion resistance, antiblocking, hydrophilic, and hydrophobic properties. Coatings formulations may exists as, Solvent-borne coatings, water-borne coatings and powder coatings.

The coatings components may be employed as: architecture coatings; OEM product coatings such as automotive coatings and coil coatings; Special Purpose coatings such as industrial maintenance coatings and marine coatings;

Typical resin types include: Polyesters, alkyds, acrylics, epoxies and polyurethanes.

Personal Care Applications

In a more specific embodiment, the low foam surfactant composition of the present invention comprises, per 100 parts by weight ("pbw") of the personal care composition, from 0.1 to 99 pbw, more preferably from 0.5 pbw to 30 pbw and still more preferably from 1 to 15 pbw of the low foam surfactant composition and from 1 pbw to 99.9 pbw, more preferably from 70 pbw to 99.5 pbw, and still more preferably from 85 pbw to 99 pbw of the personal care composition. Such amounts of low foam surfactant composition can also be used in the agrochemical composition, the coating composition, the home care composition and the oil and gas applications.

The low foam surfactant composition of the present invention may be utilized in personal care emulsions, such as shampoo and conditioners as well as lotions, and creams.

The personal care applications where the low foam surfactant composition of the present invention and the silicone compositions derived therefrom of the present invention may be employed include, but are not limited to, deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products such as nail polish, nail polish remover, nails creams and lotions, cuticle softeners, protective creams such as sunscreen, insect repellent and anti-aging products, color cosmetics such as lipsticks, foundations, face powders, eye liners, eye shadows, blushes, makeup, mascaras and other personal care formulations where silicone components have been conventionally added, as well as drug delivery systems for topical application of medicinal compositions that are to be applied to the skin.

In a more specific embodiment, the personal care composition of the present invention further comprises one or more personal care ingredients. Suitable personal care ingredients include, for example, emollients, moisturizers, humectants, pigments, including pearlescent pigments such as, for example, bismuth oxychloride and titanium dioxide coated mica, colorants, fragrances, biocides, preservatives, antioxidants, anti-microbial agents, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, such as anionic, cationic nonionic and zwitterionic surfactants, silicone oils, volatile silicones, organic oils, waxes, film formers, thickening agents such as, for example, fumed silica or hydrated silica, polyacrylates, cellulose, cellulose derivatives, particulate fillers, such as for example, talc, kaolin, starch, modified starch, mica, nylon, clays, such as, for example, bentonite and organo-modified clays.

Suitable personal care compositions are made by combining, in a manner known in the art, such as, for example, by mixing, one or more of the above components with the low foam surfactant composition. Suitable personal care compositions may be in the form of a single phase or in the form of an emulsion, including oil-in-water, water-in-oil and anhydrous emulsions where the silicone phase may be either the discontinuous phase or the continuous phase, as well as multiple emulsions, such as, for example, oil-in water-in-oil emulsions and water-in-oil-in water-emulsions.

In another useful embodiment, a skin care composition comprises the low foam surfactant composition, and a vehicle, such as, for example, a silicone oil or an organic oil. The skin care composition may, optionally, further include emollients, such as, for example, triglyceride esters, wax esters, alkyl or alkenyl esters of fatty acids or polyhydric alcohol esters and one or more the known components conventionally used in skin care compositions, such as, for example, pigments, vitamins, such as, for example, Vitamin A, Vitamin C and Vitamin E, sunscreen or sunblock compounds, such as, for example, titanium dioxide, zinc oxide, oxybenzone, octylmethoxy cinnamate, butylmethoxy dibenzoylmethane, p-aminobenzoic acid and octyl dimethyl-p-aminobenzoic acid.

In another useful embodiment, a color cosmetic composition, such as, for example, a lipstick, a makeup or a mascara composition comprises the low foam surfactant composition, and a coloring agent, such as a pigment, a water soluble dye or a liposoluble dye.

The uses of the compositions of the present invention are not restricted to personal care compositions, other products such as waxes, polishes and textiles treated with the compositions of the present invention are also contemplated.

Home Care Applications

Home care applications include laundry detergent and fabric softener, dishwashing liquids, wood and furniture polish, floor polish, tub and tile cleaners, toilet bowl cleaners, hard surface cleaners, window cleaners, antifog agents, drain cleaners, auto-dish washing detergents and sheeting agents, carpet cleaners, prewash spotters, rust cleaners and scale removers.

Oil and Gas Applications

Oil and Gas applications include emulsion control, including crude oil demulsification and emulsion prevention. Another use is foam control.

EXAMPLES

Description of Mono-Trisiloxane Alkoxylate (II)

Mono-trisiloxane alkoxylates (MTSA) (II) of the present invention are described in Table 1 and are of the general formula:

Where Q is a polyalkyleneoxide group of the general formula:

TABLE 1

| Description of the Monotrisiloxane Components | | | |
|---|---|---|---|
| ID | g | h | $R^{18}$ |
| MTSA-1 | 7.5 | 0 | OH |
| MTSA-2 | 7.5 | 0 | $CH_3$ |
| MTSA-3 | 5 | 2.5 | OH |
| MTSA-4 | 4 | 0 | OH |

Description of Polyalkyleneoxide Components

Polyalkyleneoxide (PAO) intermediates for the Di-Trisiloxane Alkoxylates of the present invention are listed in Table 2.

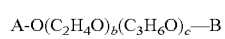

A and B are selected from H; —$CH_2CH$=$CH_2$ and —$CH_2C(CH_3)$=$CH_2$;

TABLE 2

Polyether Intermediates for Di-Trisiloxane Alkoxylates (I)

| ID | A | b | c | B |
|---|---|---|---|---|
| PAO-1 | H | 7.5 | 0 | H |
| PAO-2 | $CH_2=CHCH_2-$ | 0 | 7-8 | $-CH_2CH=CH_2$ |
| PAO-3 Comparative | $CH_2=CHCH_2-$ | 0 | 34 | $-CH_2CH=CH_2$ |
| PAO-4 | $CH_2=CHCH_2-$ | 5 | 2.5 | H |
| PAO-5 | $CH_2=CHCH_2-$ | 5 | 2.5 | $-CH_2CH=CH_2$ |
| PAO-6 | $CH_2=CHCH_2-$ | 7.5 | 0 | $-CH_2CH=CH_2$ |
| PAO-7 | $CH_2=C(CH_3)-CH_2-$ | 7.5 | 0 | $-CH_2C(CH_3)=CH_2$ |
| PAO-8 | $CH_2=CHCH_2-$ | 0 | 13 | $-CH_2CH=CH_2$ |
| PAO-9 | $CH_2=CHCH_2-$ | 3-4 | 0 | $-CH_2CH=CH_2$ |
| PAO-10 | $CH_2=CHCH_2-$ | 0 | 3 | $-CH_2CH=CH_2$ |

Example 1: Preparation Example

In-Situ Synthesis of Low Foam D: Trisiloxane Alkoxylates (DITSA-0/MTSA-3) by Dehydrocondensation.

A series of di-trisiloxane alkoxylates (DITSA) (I) were made by dehydrocondensation (DHC) of the terminal OH group on a Mono-trisiloxane alkoxylate (MTSA) with 1,1,1,3,5,5,5 heptamethyltrisiloxane ($MD^HM$). The $MD^HM$ was added at a ratio equivalent to 10, 15, 20, 30 of the hydroxyl content (mole % OH).

The MTSA, $MD^HM$ and sodium t-butoxide (300 ppm) were charged to 250 mL, 3-neck flask fitted with a reflux condenser, stirrer and thermocouple. The mixture was heated to 50° C. under nitrogen. The reaction was carried out for between 4.5 and 25 hours at 50° C. The reaction was considered complete when ≤0.2 cc H2/g was observed by an KOH/ethanol Fermentation Test. The final product was neutralized with glacial acetic acid. The product was finished with 1 g sodium bicarbonate to neutralize any excess acetic acid, and mixed for 30 minutes at 50° C. The product was then filtered and stripped under vacuum. The resulting products are a mixture of MTSA-3 and a composition of the present invention Table 3 sets forth the relative amounts of reactants used for each products by dehydrocondensation. Products of the present invention are designated as DHCB-1 through DHCB-4

TABLE 3

Reagents for the Preparation of Low Foam Compositions Obtained by DHC

| ID | MTSA-3 (g) | $MD^HM$ (g) | t-Bu—ONa (gm) | Rxn temp (° C.) | Rxn time (hr) | $CH_3COOH$ (g) |
|---|---|---|---|---|---|---|
| DHCB-1 | 78.74 | 3.00 | 0.024 | 50 | 25 | Nd |
| DHCB-2 | 78.74 | 4.51 | 0.024 | 50 | 6.5 | 0.02 |
| DHCB-3 | 78.74 | 6.01 | 0.0375 | 50 | 4.5 | 0.03 |
| DACB-4 | 78.74 | 9.01 | 0.0268 | 50 | 22 | 0.026 |

The following compositions are the "In-situ" reaction products from Table 3 and described in Tables 4 relative to the general formula:

where $R^5$ is

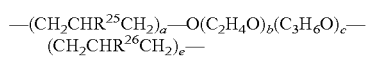

in which $R^{25}$ and $R^{26}$ are H or $CH_3$

TABLE 4

In-Situ Reaction Products of Low Foam Compositions Obtained by DHC

| ID | DiTSA-0 (%) | % MTSA-3 | a | b | c | e | $R^{25}$ | $R^{26}$ |
|---|---|---|---|---|---|---|---|---|
| DHCB-1 | 10 | 90 | 1 | 5 | 2.5 | 0 | H | H |
| DHCB-2 | 15 | 85 | 1 | 5 | 2.5 | 0 | H | H |
| DHCB-3 | 20 | 80 | 1 | 5 | 2.5 | 0 | H | H |
| DHCB-4 | 30 | 70 | 1 | 5 | 2.5 | 0 | H | H |

Preparation Example 2 (DITSA-1)

Low Foam Composition Obtained by DHC of PEG 400 (PAO-1) and $MD^HM$

The PAO-1 (50.1 g; 0.25 moles), sodium proplonate (~1000 ppm) and 6.7 g (0.03 moles) $MD^HM$ were charged to 250 mL, 4-neck flask fitted with a reflux condenser, stirrer and thermocouple. The mixture was heated to 120° C. under nitrogen. The remaining 60.4 g (0.271 moles) $MD^HM$ was added slowly via addition funnel over ~2 hours at 120° C. The reaction was considered complete when the signal for an OH peak was no longer detectable by FTIR (3,450 to 3,470 cm-1). The final product was stripped under vacuum (~30 torr) at 120° C. for 2 hours, and then cooled to ambient temperature and filtered. The resulting product, composition of the present invention, was a clear colorless, low viscosity liquid. Product ID: DiTSA-1.

Preparation Example 3 (DiTSA-2)

Low Foam Composition Obtained by Hydrosilylation of PAO-6 and $MD^HM$

The PAO-6 (150 g), and $MD^HM$ (62.04 g) were weighed into a 3-neck, 250 mL flask fitted with a reflux condenser, stirrer and thermocouple. The flask content was heated to 85° C. and catalyzed with 0.5 mL of a 1% solution of chloroplatininc acid, at which point the temperature increased to 104° C. The reaction mixture was held at this temperature for 1 hours, at which point no residual $MD^HM$ was detected by FTIR.

The product was vacuum stripped (~9 torr/121° C. for 50 minutes and then filtered. The resulting product was a clear amber liquid. Product ID: DiTSA-2.

Preparation Example 4 (DITSA-3)

Low Foam Composition Obtained by Hydrosilylation of PAO-7 and $MD^HM$

The PAO-7 (150 g), a dimethallyl terminated polyalkyleneoxide, and $MD^HM$ (67.92 g) were weighed into a 3-neck, 250 mL flask fitted with a reflux condenser, stirrer and thermocouple. The contents was heated to 85° C. and catalyzed with 0.5 mL of a 1% solution of chloroplatininc acid, at which point the temperature increased to 96° C. The reaction mixture was held at this temperature for 4 hours, at which point no residual $MD^HM$ was detected by FTIR.

The product was vacuum stripped (~10 torr/121° C. for 30 minutes and then filtered. The resulting product was a clear amber liquid. Product ID: DiTSA-3.

Preparation Examples 5-7

Preparation Examples

Below is the general procedure for the following products:

General Procedure for the preparation of DiTSA components: Examples 5-10 The PAO, $MD^HM$ and 0.1 wt % sodium propionate were weighed into a 3-neck, 250 mL flask fitted with a reflux condenser, stirrer and thermocouple. The flask content was heated to 90° C. under nitrogen blanket. The reaction mixture was catalyzed with 10 ppm chloroplatininc acid, at which point the temperature increased to ~100° C. The reaction mixture was held at this temperature for 1 hour, at which point no residual $MD^HM$ was detected by a KOH/ethanol Fermentation Test.

The product was cooled to 50° C. and neutralized with 1 g moist sodium bicarbonate and mixed for 30 minutes. The product was filtered and vacuum stripped to remove volatiles. The resulting products were clear amber liquids. Table 5 provides the reaction mixture for each of the DiTSA compositions.

Table 6 provides the compositions of the DITSA component of the present invention resulting from the reactions described in Table 5.

Summary of Examples 5-7

Example 5: Preparation of DiTSA-4: Low Foam Composition Obtained by Hydrosilylation of PAO-5 and $MD^HM$ Example 6: Preparation of DITSA-5: Low Foam Composition Obtained by Hydrosilylation of PAO-2 and $MD^HM$ Example 7: Preparation of DiTSA-6 Low Foam Composition Obtained by Hydrosilylation of (PAO-3) and $MD^HM$

TABLE 5

Reaction mixtures for DiTSA Compositions: (Examples 5-7)

| PAO | PAO (g) | $MD^HM$ (g) | CPA (g) | Product ID |
|---|---|---|---|---|
| PAO-5 | 20 | 14.3 | 0.140 | DITSA-4 |
| PAO-2 | 50.5 | 32.96 | 0.415 | DiTSA-5 |
| PAO-3 | 50 | 8.215 | 0.058 | DiTSA-6 Comparative |

(I)

where $R^5$ is

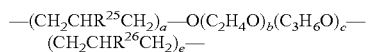

where $R^{25}$ and $R^{26}$ are H or $CH_3$

TABLE 6

Composition of Low Foam Di-Trisiloxane Alkoxylates

| ID | % DiTSA | Type (Note 1) | a | b | c | e | $R^{25}$ | $R^{26}$ |
|---|---|---|---|---|---|---|---|---|
| DiTSA-1 | 100 | Inv | 0 | 9.5 | 0 | 0 | — | — |
| DiTSA-2 | 100 | Inv | 1 | 7.5 | 0 | 1 | H | H |
| DiTSA-3 | 100 | Inv | 1 | 7.5 | 0 | 1 | $CH_3$ | $CH_3$ |
| DiTSA-4 | 100 | Inv | 1 | 5 | 2.5 | 1 | H | H |
| DiTSA-5 | 100 | Inv | 1 | 0 | 7-8 | 1 | H | H |
| DiTSA-6 | 100 | Comp | 1 | 0 | 34 | 1 | H | H |

(Note 1)-
Inv = composition of Present Invention;
Comp. = Comparative

Example 8

The Low Foam compositions (LF) of the present invention were prepared as blends of the di-trisiloxane alkoxylate component (a) (DiTSA) of the present invention with a mono-trisiloxane alkoxylate component (b) (MTSA). The blends were prepared by combining the two components in a 10 dram vial at the desired ratio and mixing until homogeneous (Table 7).

TABLE 7

DiTSA and MTSA Blend Compositions (Wt %)

| ID | LF-1 | LF-2 | LF-3 | LF-4 | LF-5 | LF-6 | LF-7 | LF-8 |
|---|---|---|---|---|---|---|---|---|
| DiTSA-2 | | | | | | | 30 | 50 |
| DiTSA-4 | 10 | 15 | 20 | | | | | |
| DiTSA-5 | | | | 5 | 10 | 15 | | |
| MTSA-3 | 90 | 85 | 80 | 95 | 90 | 85 | 70 | 50 |

| ID | LF-9 | LF-10 | LF-11 | LF-12 | LF-13 | LF-14 | LF-15 | LF-16 |
|---|---|---|---|---|---|---|---|---|
| DiTSA-2 | | 30 | 50 | | | | | |
| DiTSA-3 | | | | 30 | 50 | | | |
| DiTSA-4 | 20 | | | | | | | |
| DiTSA-1 | | | | | | 25 | 50 | |
| MTSA-1 | 80 | 70 | 50 | 70 | 50 | 75 | 50 | |
| DiTSA-6 | | | | | | | | 10 |
| MTSA-3 | | | | | | | | 90 |

| ID | LF-17 | LF-18 | LF-19 |
|---|---|---|---|
| DiTSA-2 | | 10 | 15 |
| DiTSA-6 | 15 | | |
| MTSA-3 | 85 | 90 | 85 |

Example—9: Foam Properties of Trisiloxane Alkoxylate Surfactants

The foaming properties of the DiTSA/MTSA blend compositions of the present invention were compared to the corresponding MTSA. The blends of Table 7 were prepared at 0.1 wt % in deionized water, and 200 mL of the solution were added to a 2 L graduated cylinder. The solution was sparged with nitrogen through a stainless steel fritted, at a rate of 1 L/minute for 1 minute. At this point the sparge was terminated and the foam volume was recorded Initially and at 1, 2 and 5 minutes after sparging.

Tables 8 and 9 demonstrate that the DHCB compositions (From Table 4) of the present invention, as well as the DiTSA compositions (From Tables 6 and 7) of the present invention, give improved Low Foam properties relative to the corresponding MTSA components.

TABLE 8

Low Foam Properties of Compositions
Obtained by Dehydrocondensation

| ID | DiTSA-0 (%) | MTSA-3 (%) | Initial | 1 min | 2 min | 5 min |
|---|---|---|---|---|---|---|
| DHCB-1 | 10 | 90 | 1000 | 765 | 460 | 200 |
| DHCB-2 | 15 | 85 | 995 | 625 | 600 | 180 |
| DHCB-3 | 20 | 80 | 270 | 40 | 20 | 20 |
| DHCB-4 | 30 | 70 | 225 | 20 | 20 | 20 |
| MTSA-3 | 0 | 100 | 1075 | 1025 | 880 | 540 |

TABLE 9

Foam properties of Low Foam Compositions

| ID | | Foam Volume (mL) | | |
|---|---|---|---|---|
| (% DiTSA in Blend) | Initial | 1 min | 2 min | 5 min |
| LF-1 (10% DiTSA-4) | 925 | 700 | 180 | 100 |
| LF-2 (15% DiTSA-4) | 315 | 20 | 10 | 10 |
| LF-3 (20% DiTSA-4) | 275 | 30 | 20 | 20 |
| LF-4 (5% DiTSA-5) | 440 | 50 | 40 | 40 |
| LF-5 (10% DiTSA-5) | 360 | 50 | 40 | 40 |
| LF-6 (15% DiTSA-5) | 355 | 40 | 40 | 40 |
| LF-7 (30% DiTSA-2) | 250 | 30 | 20 | 20 |
| LF-8 (50% DiTSA-2) | 210 | 20 | 20 | 20 |
| LF-16 (10% DiTSA-6) | 1065 | 1000 | 860 | 540 |
| LF-17 (15% DiTSA-6) | 1050 | 960 | 860 | 530 |
| LF-18 (10% DiTSA-2) | 1030 | 900 | 830 | 585 |
| LF-19 (15% DiTSA-2) | 700 | 275 | 100 | 60 |
| MTSA-3 (Comparative) | 1075 | 1025 | 880 | 540 |
| LF-9 (20% DiTSA-4) | 515 | 145 | 120 | 80 |
| LF-10 (30% DiTSA-2) | 1140 | 1105 | 1010 | 740 |
| LF-11 (50% DiTSA-2) | 620 | 60 | 40 | 40 |
| LF-12 (30% DiTSA-3) | 1050 | 1015 | 900 | 680 |
| LF-13 (50% DiTSA-3) | 450 | 65 | 40 | 40 |
| LF-14 (25% DiTSA-1) | 1055 | 960 | 700 | 400 |
| LF-15 (50% DiTSA-1) | 995 | 660 | 400 | 280 |
| MTSA-1 (Comparative) | 1200 | 1140 | 1020 | 700 |

Example 10: Spreading Properties of Low Foam Compositions

This examples illustrates the spreading properties of blends of the low foam compositions (DITSA component) of the present invention with an MTSA, and compared to the spreading of the corresponding MTSA.

Spreading was determined using between 0.1% and 0.4% (actives) surfactant. Solutions were prepared in Milli-Pore water (deionized) where a 10 µL drop was placed on a polystyrene surface (Petri-dish) and the spread diameter, in mm is determined after 30 seconds. Table 10 Illustrates that the spreading properties of the DHCB compositions are similar, but lower than the MTSA-3 alone (Table 10).

TABLE 10

Speading Properties of Compositions Obtained by Dehydrocondensation

| | DiTSA-0 | MTSA- | Spread Diameter (mm) | | |
|---|---|---|---|---|---|
| ID | (%) | 3 (%) | 0.05 Wt % | 0.1 Wt % | 0.2 Wt % |
| DHCB-1 | 10 | 90 | nd | 36 | Nd |
| DHCB-2 | 15 | 85 | nd | 25 | Nd |
| DHCB-3 | 20 | 80 | nd | 26 | Nd |
| DHCB-4 | 30 | 70 | nd | 26 | Nd |
| MTSA-3 (Comparative) | 0 | 100 | 32 | 44 | 48 |

As with the MTSA component alone, the loam foam (LF) compositions made by hydrosilylation and blended with a MTSA (Table 7), provide enhanced spreading spreading relative to non-silicone surfactants TAE (Ethomeen T25; Tallow Amine Ethoxylate with 15 EO units; AlzoNobel) and OPE (Triton X-100; Octylphenolethoxylate with 10 EO units, Dow Chemical) When the DITSA component is present at less than or equal to 20 wt %, spreading is comparable to the MTSA alone. Although increased spreading is observed, relative to the TAE or OPE, when the DITSA component is used at a higher ratio (MTSA/DITSA), spreading appears to decrease with an increase in DiTSA in the LF compositions (Table 11).

TABLE 11

Spreading Properties of Low Foam Compositions

| ID | | Spread Diameter (mm) | |
|---|---|---|---|
| (% DiTSA in Blend) | 0.05 Wt % | 0.1 Wt % | 0.2 Wt % |
| LF-1 (10% DiTSA-4) | 23 | 35 | 44 |
| LF-2 (15% DiTSA-4) | 23 | 37 | 45 |
| LF-3 (20% DiTSA-4) | 21 | 36 | 45 |
| LF-4 (5% DiTSA-5) | 31 | 44 | 48 |
| LF-5 (10% DiTSA-5) | 29 | 43 | 45 |
| LF-6 (15% DiTSA-5) | 27 | 36 | 46 |
| LF-18 (10% DiTSA-2) | nd | 40 | Nd |
| LF-19 (15% DiTSA-2) | nd | 25 | Nd |
| LF-7 (30% DiTSA-2) | 10 | 14 | 26 |
| LF-8 (50% DiTSA-2) | 11 | 10 | 11 |
| LF-16 (10% DiTSA-6) | nd | 43 | Nd |
| LF-17 (15% DiTSA-6) | nd | 43 | Nd |
| MTSA-3 (Comparative) | 32 | 44 | 48 |
| Ethomeen T/25 | nd | nd | 5 |
| Triton X-100 | nd | nd | 7 |

Example 11: In-Situ Preparation of MTSA-3/DITSA-4 Blend

This example illustrates that it is possible to generate the low foam composition of the present invention by hydrosilylation of a polyalkyleneoxide with terminal unsaturation, such as allyl, methallyl or vinyl, along with a monosubstituted allylpolyalkyleneoxide. For example, a mixture of PAO-4 with PAO-5 (Table 2), at a ratio to deliver the desired DITSA component of the present invention, may be co-reacted with $MD^HM$ to yield a mixed trisiloxane alkoxylate composition containing MTSA-3 and DiTSA-4: Contained at a level of 15% (LF-20), 20% (LF-21) and 25% (LF-22).

The PAO, $MD^HM$ and 0.1 wt % sodium propionate were weighed into a 3-neck, 250 mL flask fitted with a reflux condenser, stirrer and thermocouple. The flask content was heated to 90° C. under nitrogen blanket. The reaction mixture was catalyzed with 10 ppm chloroplatininc acid, at which point the temperature increased to ~100° C. The reaction mixture was held at this temperature for 1 hour, at which point no residual $MD^HM$ was detected by a KOH/ethanol "Fermentation Test".

The product was cooled to 50° C. and neutralized with 1 g moist sodium bicarbonate and mixed for 30 minutes. The product was filtered and vacuum stripped to remove volatiles. The resulting products were clear amber liquids.

Spreading:

The products provide enhanced spreading similar to the MTSA-3 (Table 12). Spreading was determined as outlined in Example 10. However, as the concentration of the DiTSA-4 Increases there is a slight reduction in spreading, which may be the result of a reduced MTSA-3 concentration in the blend. For example a 0.1% solution of LF-22 delivers 0.025% DiTSA-4 and 0.075% MTSA-3.

TABLE 12

Spreading properties of "In-Situ" MTSA-3/DiTSA-4 Blends

| In-Situ Blend ID | MTSA-3 (Wt %) | DiTSA-4 (Wt %) | 0.05 Wt % | 0.1 Wt % | 0.2 Wt % |
|---|---|---|---|---|---|
| LF-20 | 85 | 15 | 24 | 35 | 48 |
| LF-21 | 80 | 20 | 26 | 36 | 48 |
| LF-22 | 75 | 25 | 24 | 34 | 46 |
| MTSA-3 (Comparative) | 100 | 0 | 32 | 44 | 48 |

Foam Properties:

The LF compositions made "In-situ" provide improved low foam properties relative to the corresponding MTSA-3. Table 13 illustrates that DITSA-4 even at levels as low as 15 wt % in the blend with MTSA-3, gives significantly less foam than the MTSA-3 alone at equivalent use rates.

TABLE 13

Foam properties of "In-situ" mixtures of MTSA-3 and DiTSA-4

| In-Situ Blend ID | MTSA-3 (Wt %) | DiTSA-4 (Wt %) | Initial | 1 min. | 2 min. | 5 min. |
|---|---|---|---|---|---|---|
| LF-20 | 85 | 15 | 315 | 30 | 30 | 20 |
| LF-21 | 80 | 20 | 460 | 50 | 50 | 40 |
| LF-22 | 75 | 25 | 325 | 30 | 30 | 20 |
| MTSA-3 (Comparative) | 100 | 0 | 1075 | 1025 | 880 | 540 |

Example 12: Uptake of 2,4-D Amine into Canola Leaf

Effect of the Low Foam (LF) component on Uptake of $^{14}C$-2,4-D Dimethylamine salt into canola leaf was determined at 2 and 24 hours after treatment (HAT) according to the method described by Lui, in Pro. 18th Asian-Pacific Weed Sci. Soc. Conf., pp. 561-566. Liu, Z Q; 2001. to establish the impact of surfactant on the speed of uptake. Surfactant was used at 0.1% for all treatments. Uptake was determined on adaxial surface of youngest fully expanded leaf. Table 14 demonstrates that the LF composition of the present invention significantly enhances glyphosate uptake at 24 HAT relative to the corresponding MTSA-3.

TABLE 14

Uptake of 2,4-D DMA (1% a.e./100 L/ha) into canola at 2 & 24 h after treatment

| Treatment | DiTSA (Wt %) | MTSA-3 (Wt %) | 2,4-D Amine Uptake % | |
|---|---|---|---|---|
| | | | 2 hat | 24 hat |
| LF-1 | 10 | 90 | 16.2 c | 61.8 a |
| LF-2 | 15 | 85 | 8.6 c | 61.5 a |
| LF-3 | 20 | 80 | 11.4 c | 59.5 a |
| LF-4 | 5 | 95 | 16.1 c | 62.5 a |
| LF-5 | 10 | 90 | 16.9 c | 60.5 a |
| LF-6 | 15 | 85 | 16.0 c | 58.2 ab |
| Comparative | 0 | 100 | 14.0 c | 49.4 b |

Note:
Results sharing a common postscript are not statistically different (p = 0.05)

Example 13: Preparation of DITSA Components by Hydrosilylation

Additional DiTSA components of the present invention were prepared by hydrosilylation in a similar fashion to those prepared in Examples 5-7.
Brief Description of the DiTSA Components
DiTSA-7:
The reaction product of PAO-8 (Diallyl-terminated polypropyleneoxide containing 13 PO units), with heptamethyltrisiloxane ($MD^HM$)
DiTSA-8:
The reaction product of PAO-9 (Diallyl-terminated polypropyleneoxide containing ~4 EO units), with heptamethyltrisiloxane ($MD^HM$)
DiTSA-9:
The reaction product of PAO-10 (Diallyl-terminated polypropyleneoxide containing 3 PO units), with heptamethyltrisiloxane ($MD^HM$)

The description of the DITSA components of the present invention are listed in Table 15, and are represented by the general structure (IA):

$$[(CH_3)_3SiO]_2Si(CH_3)-R^5-Si(CH_3)[OSi(CH_3)_3]_2 \quad (IA)$$

where $R^5$ is $$-(CH_2CHR^{25}CH_2)_a-O(C_2H_4O)_b(C_3H_6O)_c-(CH_2CHR^{26}CH_2)_e-$$

where $R^{25}$ and $R^{26}$ are H or $CH_3$

TABLE 15

General Description of DiTSA Components

| ID | DiTSA (%) | a | b | c | e | $R^{25}$ | $R^{26}$ |
|---|---|---|---|---|---|---|---|
| DiTSA-7 | 100 | 1 | 0 | 13 | 1 | H | H |
| DiTSA-8 | 100 | 1 | 3-4 | 0 | 1 | H | H |
| DiTSA-9 | 100 | 1 | 0 | 3 | 1 | H | H |

Example 14: Additional MTSA/DiTSA Blend Compositions

Physical blends of MTSA-3 with the DiTSA components of the present invention were prepared by combining 1 g of the DITSA with 9 g MTSA-3 in a vial and mixing until homogeneous.

The foam suppression properties were determined as outlined in Example 9 for 0.1% solutions of the blends, and compared to MTSA-3 alone at 0.1%.

Table 16 demonstrates that the DiTSA compositions of the present invention provide foam suppression of MTSA-3 when incorporated at the 10% blend level, indicating that these materials are highly efficient at suppressing foam.

TABLE 16

Foam Properties of MTSA/DiTSA Blends

| ID | Ratio (MTSA/DiTSA) | Foam Volume (mL) | | | |
|---|---|---|---|---|---|
| | | Initial | 1 min. | 2 min. | 5 min. |
| MTSA-3/DiTSA-7 | 90/10 | 410 | 50 | 50 | 40 |
| MTSA-3/DiTSA-8 | 90/10 | 455 | 30 | 20 | 10 |
| MTSA-3/DiTSA-9 | 90/10 | 305 | 30 | 30 | 10 |

TABLE 16-continued

Foam Properties of MTSA/DiTSA Blends

| ID | Ratio (MTSA/ DiTSA) | Foam Volume (mL) | | | |
|---|---|---|---|---|---|
| | | Initial | 1 min. | 2 min. | 5 min. |
| DiTSA-4 (Alone) | 0/100 | 505 | 10 | 10 | 5 |
| MTSA-3 (Comparative) | 100/0 | 1075 | 1025 | 880 | 540 |

Example 15

The Impact of MTSA/DITSA concentration on foam suppression was determined as outlined in Example 9, with the exception that the surfactant concentration was at a lower level (0.025% and 0.05%) demonstrating that the DiTSA composition of the present invention is robust enough to suppress foam even at low levels. This is shown in Table 17, where a blend of MTSA-3 (85%) and DiTSA-4 (15%) provide significantly lower foam than achievable with the MTSA-3 alone at corresponding concentrations.

TABLE 17

Foam Properties of MTSA/DiTSA Blends

| Wt % | Time | Foam Volume (mL) | | Reduction[a] (%) |
|---|---|---|---|---|
| | | MTSA-3 | MTSA-3/DiTSA-4 | |
| 0.025% | Initial | 1120 | 400 | 64% |
| 0.025% | 1 min. | 1085 | 90 | 92% |
| 0.025% | 2 min. | 1060 | 80 | 92% |
| 0.025% | 5 min. | 980 | 50 | 95% |
| 0.05% | Initial | 1010 | 430 | 57% |
| 0.05% | 1 min. | 920 | 30 | 97% |
| 0.05% | 2 min. | 800 | 30 | 96% |
| 0.05% | 5 min. | 380 | 20 | 95% |

[a]Reduction of foam for MTSA-3/DiTSA-4 blend relative to MTSA-3 alone.

Example 16

This example demonstrates that the inclusion of a hydrophobized silica particle in combination with the DiTSA composition of the present invention, improves the suppression of foam relative to the same MTSA-1/DiTSA-4 blend (75/25 ratio), without the silica.

Test solutions (200 mL) were prepared in deionized water at 0.1%, and then poured into a 2000 mL graduated glass cylinder. The solution was foamed with a 10 μm stainless steel fritt, with nitrogen at 1 liter/min rate, controlled by a flow regulator.

When the foam+liquid volume reached 600 or 400 mL, respectively, the gas flow was stopped and the stopwatch started. The time of abrupt foam collapse was measured in seconds.

Table 18 demonstrates that the inclusion of silica with the DITSA-4 component significantly reduces the collapse time of the foam relative to the same mixture without silica.

TABLE 18

Impact of Silica addition to DiTSA-4 on Foam Supression

| MTSA-1 (75%) + DiTSA-4 (25%) (0.1 wt % Blend) Foam volume/Time (sec) | | MTSA-1 (75%) + DiTSA-4 (25%) + Silica (4%)[a] (0.1 wt % Blend) Foam volume/Time (sec) | |
|---|---|---|---|
| 600 mL | 400 mL | 600 mL | 400 mL |
| 137.5 | 230.7 | 40.2 | 76.3 |

[a]Silica - Aerosil R-812S

Example 17

This example demonstrates that the Low foam compositions of the present invention improve the herbicide efficacy of glyphosate-Isopropylamine (Gly-IPA) on Velvetleaf (*Abutilion theophrasti*) relative to the MTSA-3 analogue alone.

Velvetleaf plants were grown from seed Indoor, under full sunlight intensity lamps, in individual pots, and then thinned to one plant per pot. Plants were fertilized as necessary (NPK 20-20-20). Glyphosate spray applications were applied when the plants reached the 3-4 true leaf stage.

Velvetleaf was treated with 1.0 wt % Gly-IPA, with and without adjuvant, at a spray volume equivalent to 100 L/ha. When adjuvant was included, it was included in the spray at 0.1 wt %. Applications were made using a track sprayer with a TeeJet 8002 nozzle. Simulated rain (2.5 cm) was applied 2 hours after treatment. Glyphosate efficacy was determined 7 and 14 days after treatment (DAT), using a visual scale of 0-100%, where 0 indicates no effect and 100 Indicates total weed control.

Table 19 demonstrates that the low foam compositions of the present invention (LF) improved the control of the weed velvetleaf better than the corresponding MTSA-3, component (b) or glyphosate-IPA alone.

TABLE 19

Effect of Adjuvant on Glyphosate-IPA Efficacy on Velvetleaf[a]

| Adjuvant | Ratio | 7 DAT | 14 DAT |
|---|---|---|---|
| LF-20[b] | 85/15 | 70 | 83 |
| LF-12[b] | 80/20 | 63 | 63 |
| LF-22[b] | 75/25 | 60 | 65 |
| LF-18[c] | 90/10 | 60 | 70 |
| MTSA-3 | NA | 50 | 47 |
| None[d] | NA | 33 | 37 |

[a]*Abutilion theophrasti*
[b]In-Situ blend made by hydrosilylation of the heptamethyltrisiloxane with PAO-4 and PAO-5-See Example 11
[c]LF-18 is a physical blend of MTSA-3 and DiTSA-2 (Table 7)
[d]None means: Glyphosate-IPA at 1% alone While the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention but that the invention will include all embodiments falling within the scope of the appended claims.

The invention claimed is:

1. A low foam surfactant composition comprising
a) di-trisiloxane alkoxylate component of formula (I):

$$(R^1R^2R^3SiO)_2(R^4)Si-R^5-Si(R^6)(OSiR^7R^8R^9)_2 \quad (1)$$

where $R^1$, $R^2$, $R^3$, $R^4$, $R^6$, $R^7$, $R^8$ and $R^9$ each independently is methyl, ethyl or linear or branched monovalent hydrocarbon radical of 3 or 4 carbon atoms,
$R^5$ is a divalent polyalkyleneoxide group of the structure:

$$-(R^{10})_aO(C_2H_4O)_b(C_3H_6O)_c(C_4H_8O)_d-(R^{11})_e-$$

where $R^{10}$ and $R^{11}$ each independently is a linear or branched divalent hydrocarbon radical of from 2 to 6 carbon atoms, a and e each independently is 0 or 1, b is 0 or greater, c is 1 or greater, and d is 0 or greater, provided that $1 \leq b+c+d \leq 20$; and,
b) mono-trisiloxane alkoxylate component of formula (II):

$$(R^{12}R^{13}R^{14}SiO)_2Si(R^{15})R^{16} \quad (11)$$

where $R^{12}$, $R^{13}$, $R^{14}$ and $R^{15}$ each independently is a linear or branched monovalent hydrocarbon radical of from 1 to 4 carbon atoms, and
$R^{16}$ is a monovalent polyalkyleneoxide group of the structure:

$$-R^{17}O(C_2H_4O)_g(C_3H_6O)_h(C_4H_8O)_i-R^{18}$$

where $-R^{17}$ is a linear or branched divalent hydrocarbon radical of from 2 to 6 carbon atoms,
$R^{18}$ is hydrogen, monovalent hydrocarbon radical of from 1 to 4 carbon atoms or acetyl, and g, h and i each independently is 0 or greater, provided that $1 \leq g+h+i \leq 15$;
and, wherein di-trisiloxane alkoxylate (I) is soluble in mono-trisiloxane alkoxylate (II).

2. The low foam surfactant composition of claim 1 wherein in formula (I), $R^1$, $R^2$, $R^3$, $R^4$, $R^6$, $R^7$, $R^8$ and $R^9$ are methyl, divalent polyalkyleneoxide group $R^5$ is such that $R^{10}$ and $R^{11}$ each independently is a hydrocarbon radical of 3 or 4 carbon atoms, a and e are 1, b is 4 to 6, c is 1.5 to 3 and d is 0 or 1; and in formula (II), $R^{12}$, $R^{13}$, $R^{14}$ and $R^{15}$ are methyl, $R^{17}$ is a hydrocarbon radical of 3 or 4 carbon atoms, $R^{18}$ is hydrogen, g is 4 to 6, h is 1.5 to 3 and i is 0.

3. The low foam surfactant composition of claim 1 wherein in formula (I), $R^1$, $R^2$, $R^3$, $R^4$, $R^6$, $R^7$, $R^8$ and $R^9$ are methyl, divalent polyalkyleneoxide group $R^5$ is such that $R^{10}$ and $R^{11}$ each independently is a hydrocarbon radical of 3 or 4 carbon atoms, a and e are 1, b is 0 or 1, c is 1 to 8 and d is 0 or 1; and in formula (II), $R^{12}$, $R^{13}$, $R^{14}$ and $R^{15}$ are methyl, $R^{17}$ is a hydrocarbon radical of 3 or 4 carbon atoms, $R^{18}$ is hydrogen, g is 4 to 6, h is 1.5 to 3 and i is 0.

4. The low foam surfactant composition of claim 3 wherein c is 1 to 4.

5. The low foam surfactant composition of claim 1 wherein in formula (I), $R^1$, $R^2$, $R^3$, $R^4$, $R^6$, $R^7$, $R^8$ and $R^9$ are methyl, divalent polyalkyleneoxide group $R^5$ is such that $R^{10}$ and $R^{11}$ each independently is a hydrocarbon radical of 3 or 4 carbon atoms, a and e are 1, b is 1 to 4, c is 1 and d is 0 or 1; and in formula (II), $R^{12}$, $R^{13}$, $R^{14}$ and $R^{15}$ are methyl, $R^{17}$ is a hydrocarbon radical of 3 or 4 carbon atoms, $R^{18}$ is hydrogen, g is 4 to 6, h is 1.5 to 3 and i is 0.

6. The low foam surfactant composition of claim 1 wherein in formula (I), $R^1$, $R^2$, $R^3$, $R^4$, $R^6$, $R^7$, $R^8$ and $R^9$ are methyl, divalent polyalkyleneoxide group $R^5$ is such that $R^{10}$ and $R^{11}$ each independently is a hydrocarbon radical of 3 or 4 carbon atoms, a and e are 1, b is 4 to 8, c is 1.5 to 3 and d is 0 or 1; and in formula (II), $R^{12}$, $R^{13}$, $R^{14}$ and $R^{15}$ are methyl, $R^{17}$ is a hydrocarbon radical of 3 or 4 carbon atoms, $R^{18}$ is hydrogen, g is 6 to 8, and h and i are 0.

7. The low foam surfactant composition of claim 1 wherein in formula (I), $R^1$, $R^2$, $R^3$, $R^4$, $R^6$, $R^7$, $R^8$ and $R^9$ are methyl, divalent polyalkyleneoxide group $R^5$ is such that a and e are each 0, b is 4 to 8, c is 1.5 to 3, and d is 0 or 1; and in formula (II), $R^{12}$, $R^{13}$, $R^{14}$ and $R^{15}$ are methyl, $R^{17}$ is a hydrocarbon radical of 3 or 4 carbon atoms, $R^{18}$ is hydrogen, g is 6 to 8, and h and i are 0.

8. The low foam surfactant composition of claim 1 wherein in formula (I), $R^1$, $R^2$, $R^3$, $R^4$, $R^6$, $R^7$, $R^8$ and $R^9$ are each methyl, divalent polyalkyleneoxide group $R^5$ is such that $R^{10}$ and $R^{11}$ each independently is a hydrocarbon radical of 3 or 4 carbon atoms, a and e are 1, b is 6 to 9, c is 1 and d is 0; and wherein component (b) each of $R^{12}$, $R^{13}$, $R^{14}$ and $R^{15}$ are methyl, $R^{17}$ is a hydrocarbon radical of 3 to 4 carbon atoms, $R^{18}$ is hydrogen, subscript g is 6 to 8, subscript h and i are each 0.

9. The low foam surfactant composition of claim 1 wherein in formula (I) $R^5$ is of the formula $$-(CH_2CH(R^{25})CH_2)_a-O(C_2H_4O)_b(C_3H_6O)_c-(CH_2CH(R^{26})CH_2)_e-$$

where subscripts a, b, c and e are as defined, and $R^{25}$ and $R^{26}$ are each independently hydrogen or methyl.

10. The low foam surfactant composition of claim 9 wherein in $R^5$, b is 0 or from 4 to about 10 and c is from 1 to about 9.

11. The low foam surfactant composition of claim 10 wherein in $R^5$, a is 1, b is 5, c is 2.5 and e is 0 and $R^{25}$ and $R^{26}$ are hydrogen.

12. The low foam surfactant composition of claim 1 wherein component (a) is present in an amount of from about 5 to about 95 weight % and component (b) is present in an amount of from about 5 to about 95 weight % based on the combined weight of components (a) and (b).

13. The low foam surfactant composition of claim 1 wherein component (a) is present in an amount of from about 10 to about 30 weight % and component (b) is present in an amount of from about 70 to about 90 weight % based on the combined weight of components (a) and (b).

14. A method of making the low foam surfactant composition of claim 1 comprising combining:
a) di-trisiloxane alkoxylate component of the formula (I):

$$(R^1R^2R^3SiO)_2(R^4)Si-R^5-Si(R^6)(OSiR^7R^8R^9)_2 \quad (1)$$

where $R^1$, $R^2$, $R^3$, $R^4$, $R^6$, $R^7$, $R^8$ and $R^9$ each independently is methyl, ethyl or linear or branched monovalent hydrocarbon radical of 3 or 4 carbon atoms,
$R^5$ is a divalent polyalkyleneoxide group having the structure:

$$-(R^{10})_aO(C_2H_4O)_b(C_3H_6O)_c(C_4H_8O)_d-(R^{11})_e-$$

where $R^{10}$ and $R^{11}$ each independently is a linear or branched divalent hydrocarbon radical of from 2 to 6 carbon atoms, a and e each independently is 0 or 1, b is 0 or greater, c is 1 or greater, and d is 0 or greater, provided that $1 \leq b+c+d \leq 20$; with
b) mono-trisiloxane alkoxylate component of the formula (11):

$$(R^{12}R^{13}R^{14}SiO)_2Si(R^{15})R^{16} \quad (11)$$

where $R^{12}$, $R^{13}$, $R^{14}$ and $R^{15}$ each independently is a linear or branched monovalent hydrocarbon radical of from 1 to 4 carbon atoms, and $R^{16}$ is a monovalent polyalkyleneoxide group of the structure:

$$-R^{17}O(C_2H_4O)_g(C_3H_6O)_h(C_4H_8O)_i-R^{18}$$

where —$R^{17}$ is a divalent hydrocarbon radical containing from 2 to 6 carbon atoms, $R^{18}$ is hydrogen, vinyl, allyl, methallyl, propenyl, monovalent hydrocarbon radical of from 1 to 4 carbon atoms or acetyl, and subscripts g, h and i each independently is 0 or greater, provided that $1 \le g+h+i \le 15$;

wherein di-trisiloxane alkoxylate (I) is soluble in mono-trisiloxane alkoxylate(II).

15. The low foam surfactant composition of claim 1 obtained by the hydrosilylation process which comprises reacting a mixture of diolefinically-modified polyalkylene oxide of formula (V):

$$R^{22}O(C_2H_4O)_k(C_3H_6O)_m(C_4H_8O)_p-R^{23} \quad (V)$$

where k, m and p are ≤0 provided that $1 \le k+m+p \le 20$, and where $R^{22}$ and $R^{23}$ each independently is an olefinically modified group of the structure:

$$CH_2=C(R^{24})-(CH_2)_r-$$

where $R^{24}$ is hydrogen or methyl and subscript r is 0 to 4, and mono alkenyl-terminated polyalkylene oxide component of formula (VI):

$$CH_2=C(R^{21})-(CH_2)_r-O-(C_2H_4O)_k(C_3H_6O)_m(C_4H_8O)_p-R^{18} \quad (VI)$$

where $R^{18}$ is hydrogen, monovalent hydrocarbon radical of from 1 to 4 carbon atoms or acetyl, $R^{21}$ is hydrogen or methyl, and k, m and p are as defined, and r is 0 to 4, with 1,1,1,3,5,5,5-heptaalkyltrisiloxane wherein the alkyl groups each independently contains from 1 to 4 carbon atoms, in the presence of a hydrosilylation catalyst, the hydrosilylation producing a mixture of component (a) of formula (I) and component (b) of formula (II).

16. The low foam surfactant composition of claim 15 where at least 5 percent of the $R^{18}$ groups is hydrogen, the process employing an excess of 1,1,1,3,5,5,5-heptaalkyltrisiloxane and a dehydrocondensation catalyst, wherein the excess 1,1,1,3,5,5,5-heptaalkyltrisiloxane reacts with terminal hydroxyl groups of formula (VI) to produce in situ a mixture of component (a) of formula (I) and component (b) of formula (II).

17. The low foam surfactant composition of claim 16 wherein hydrosilylation reaction product (b) of formula (II) is such that $R^{18}$ is hydrogen and at least a portion of same is then reacted with 1,1,1,3,5,5,5-heptaalkyltrisiloxane wherein the alkyl groups each independently contains from 1 to 4 carbon atoms to produce hydrosilylation reaction product (a) of formula (I).

18. The low foam surfactant composition of claim 1 further comprising an agrochemical active ingredient.

19. The low foam surfactant composition of claim 18 wherein the agrochemical active ingredient is one or more of a herbicide, insecticide, fungicide, growth regulator, micronutrient or fertilizer.

20. A crop or plant having the agrochemical composition of claim 18 applied thereto.

21. The low foam surfactant composition of claim 1 as a component of a coating composition, personal care composition, home care composition or composition for oil or gas application.

22. The low foam surfactant composition of claim 1 which has a level of foam that is less than 1,000 ml of foam, when 200 ml of a 0.1 wt % amount of the low foam surfactant composition is added to a 2 L graduated cylinder wherein the composition is a solution that is subjected to a nitrogen sparge through the solution through a stainless steel fit at a rate of 1 L per minute for one minute.

23. The low foam surfactant composition of claim 1, comprising an amount of the di-trisiloxane alkoxylate component of formula (I) effective to reduce the amount of foam produced by the mono-trisiloxane alkoxylate component of formula (II), in the absence of the di-trisiloxane alkoxylate component.

24. The low foam surfactant composition of claim 23, wherein the composition has a level of foam that is less than a surfactant composition that contains only the mono-trisiloxane alkoxylate component by at least 50% when measured by a test in which 200 ml of a 0.1 wt % amount of the low foam surfactant composition is added to a 2 L graduated cylinder wherein the composition is a solution that is subjected to a nitrogen sparge through the solution through a stainless steel fit at a rate of 1 L per minute for one minute and permitted to settle for one minute thereafter.

* * * * *